United States Patent [19]

Lapicola et al.

[11] Patent Number: 4,745,071

[45] Date of Patent: May 17, 1988

[54] METHOD FOR THE VOLUMETRIC DIFFERENTIATION OF BLOOD CELLS TYPES

[75] Inventors: James D. Lapicola, Pleasant Hill; Sherburne M. Edmondson, Jr., Cupertino, both of Calif.

[73] Assignees: Sequoia-Turner Corporation, Mountain View, Calif.; Hematology Marketing Associates, Inc., Plano, Tex.

[21] Appl. No.: 914,637

[22] Filed: Oct. 2, 1986

Related U.S. Application Data

[62] Division of Ser. No. 772,666, Sep. 5, 1985, abandoned.

[51] Int. Cl.[4] ............................................. G01N 33/50
[52] U.S. Cl. ....................................... 436/63; 436/17; 436/18
[58] Field of Search ......................... 436/10, 17, 18, 63

[56] References Cited

U.S. PATENT DOCUMENTS

| | | | |
|---|---|---|---|
| 2,745,826 | 5/1956 | Semenoff et al. | 260/96.5 T |
| 3,236,733 | 2/1966 | Karsten et al. | 514/188 |
| 3,281,366 | 10/1966 | Judge et al. | 252/107 |
| 3,874,852 | 4/1975 | Hamill | 436/66 X |
| 4,099,917 | 7/1978 | Kim | 436/10 |
| 4,185,964 | 1/1980 | Lancaster | 436/10 X |
| 4,213,876 | 7/1980 | Crews et al. | 436/18 |
| 4,271,123 | 6/1981 | Curry et al. | 422/67 X |
| 4,286,963 | 9/1981 | Ledis et al. | 436/63 |
| 4,346,018 | 8/1982 | Carter et al. | 436/17 |
| 4,485,175 | 11/1984 | Ledis et al. | 436/63 |
| 4,493,821 | 1/1985 | Harrison | 436/17 X |
| 4,521,518 | 6/1985 | Carter et al. | 436/63 |
| 4,528,158 | 7/1985 | Gilles et al. | 422/63 |
| 4,529,705 | 7/1985 | Larsen | 436/63 X |
| 4,617,275 | 10/1986 | Matsuda et al. | 436/10 |

FOREIGN PATENT DOCUMENTS

84/03771  9/1984  World Int. Prop. O. ............ 436/63

OTHER PUBLICATIONS

Bessman, Tex. Med., vol. 80, pp. 33–35, 1984.
Allen et al., Am. J. Clin. Path., vol. 33, pp. 553–556, 1960.
Van Dilla et al., I.V.P.S.E.B.M., vol. 125, pp. 367–370, 1967.
Hatch et al., Am. J. Clin. Path., vol. 36, pp. 220–223, 1960.
Davis et al., J. Med. Lab. Technol., vol. 26, pp. 26–30, 1969.
Cox et al., Am. J. Clin. Path., vol. 84, No. 3, pp. 297–305, 9/85.
D'Angelo et al., Am. J. Clin. Path., vol. 34, pp. 220–223, 1961.
Adams et al., Phip. Med. Biol., vol. 12, pp. 79–92, 1967.
Torlontano et al., Acta Haemat., vol. 45, pp. 325–329, 1971.
Saslow, "The Volume of Rabbit Erythrocytes in Solutions of Various Tonicities", PhD. Thesis, New York University, 1931.
Wintrobe, ed., *Clinical Hematology*, 6th edition, Lea & Febiger, Philadelphia, 1974, Chapter One: "The Approach to Hematologic Problems".
Miale, *Laboratory Medicine: Hematology*, 4th edition, C. V. Mosby Co., St. Louis, 1972, Chapter 3, "Morphology of blood and bone marrow cells", Chapter 13, "Leukocytes and Diseases of Leukopoieses".
Ponder, *Hemolysis and Related Phenomena*, Second edition, Grune & Stratton, New York, 1971.
Taylor et al., J. Clin. Path., vol. 13, p. 249, 1960.
Humphries et al., Ser. Haemat., vol. V, No. 2, pp. 142–162, 1972.

*Primary Examiner*—Barry S. Richman
*Assistant Examiner*—Robert J. Hill, Jr.
*Attorney, Agent, or Firm*—Limbach, Limbach & Sutton

[57] ABSTRACT

Improved reagents and methods for obtaining distinct volumetric differentiation of platelets, erythrocytes and certain leukocyute subpopulations are disclosed. 1,3-dimethylurea is disclosed as a cell stabilizing agent for use in the blood diluent reagent. A hematology analyzer detergent is described wherein the addition of a wetting agent to the diluent of the instant invention provides the necessary attributes of an automatic analyzer detergent. The lysing reagent exploits the selective and intrinsically gentle lytic qualities of the dodecyl quaternary ammonium salt. The improved method modifies the leukocytes so that the frequent lymphocyte and neutrophil subpopulations are well separated on a volume scale, permitting quantitative evaluation of infrequent and rare leukocyte subpopulations as well as improved enumeration of the lymphocytes and neutrophils.

8 Claims, 2 Drawing Sheets

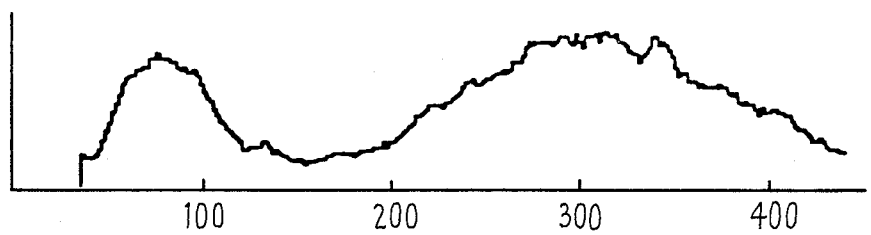
FIG._2
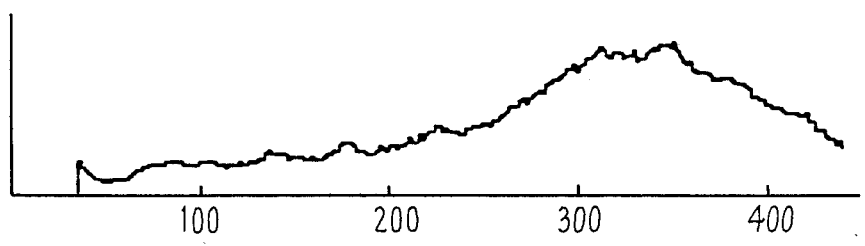
FIG._3
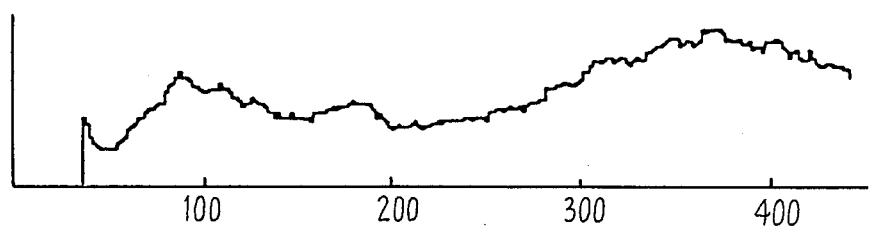
FIG._4
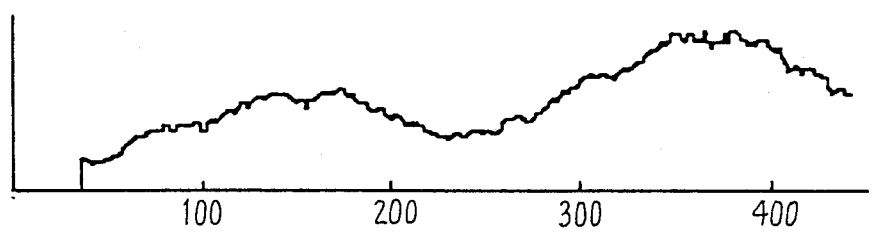
FIG._5
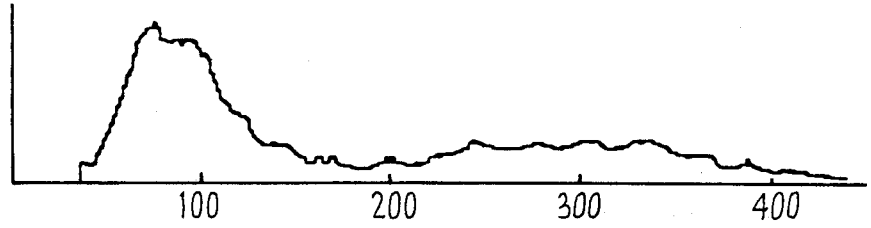
FIG._6

METHOD FOR THE VOLUMETRIC DIFFERENTIATION OF BLOOD CELLS TYPES

This is a division of application Ser. No. 772,666, filed 9-5-85, now abandoned.

TECHNICAL FIELD

This invention relates generally to hematology and the use of automated analytical equipment therein, and more particularly to improved lysing reagents, diluent reagents and detergents, and their method of use in connection with such automated equipment.

BACKGROUND OF THE INVENTION

Since many diseases primarily affect the blood, or blood system, and since many other disorders result in alterations in the blood, hematological analysis, in conjunction with traditional diagnostic techniques, provides a useful clinical tool for the recognition and treatment of many diseases. The automation of this analysis has made its use widespread and commonplace. The compositions and methods of this invention are useful in automated hematological analyses.

In healthy man the circulating blood contains three major categories of cells: a population of small thrombocytes (or platelets) typically around 10 fl in average volume and around 150,000 to 400,000/ul in numerical concentration, the hemoglobin-carrying population of erythrocytes (or red cells) typically around 90 fl in average volume and around 4,000,000 to 6,000,000/ul in numerical concentration, and the population of larger nucleated leukocytes (or white cells). The leukocyte category consists of two numerically predominant or frequent subpopulations (the smaller monomorphonuclear lymphocytes and the larger polymorphonuclear neutrophilic granulocytes—each typically in the range of 1,000 to 5,000/ul in numerical concentration) and three infrequent subpoplulations (the monomorphonuclear monocytes, the polymorphonuclear eisinophilic granulocytes, and the polymorphonuclear basophilic granulocytes each typically below 500/ul in numerical concentration).

In many diseases the three infrequent leukocyte subpopulations tend to be more plentiful. Additionally, in disease, several other even less frequent or anomalous leukocyte subpopulations may appear in the blood in noticeable concentrations. The compositions and methods of this invention permit the enumeration of the two frequent leukocyte subpopulations together with a powerful quantitative screening evaluation of the remaining infrequent physiologic and rare pathologic leukocyte subpopulations.

Electronic cell counters are used in the enumeration of all these blood cell categories.

This enumeration and screening evaluation is achieved by lysing away all the extremely numerous and therefore obscuring erythrocytes (as is usual for resistivity leukocyte counting) and by simultaneously modifying the frequent (and also obscuring) lymphocyte and neutrophil subpopulations so that in terms of relative resistivity size, the lymphocytes are moved further below the infrequent subpopulation cells and the neutrophils are moved further above the infrequent subpopulation cells than are the native unmodified leukocytes of the circulating blood. In this way the two frequent leukocyte subpopulations are drawn apart (as shown in FIG. 1) to expose a clear stage on which pathophysiologic increases of any of the infrequent and rare subpopulations are readily apparent and can be evaluated quantitatively.

From 1960 onwards, it was shown that the use of the proper red cell lysing agent could result in distinguishing white cell subpopulations. See, e.g., Allen, J. D., and Gudaitis, A. V., "Diluting Fluid for Electronic Counting of Leukocytes and Hemoglobin Determinations", Am. J. Clin. Path., 33, 553–556 (1960); Van Dilla, M. A., Fulwyler, M. J. and Boone, I. U., P.S.E.B.M., 125, 367–370 (1967). In these early experiments saponin (sapogenin glycosides) was used as the red cell lysing agent. Unfortunately, saponin required forty-five seconds or more for effective hemolysis. Measurements taken prior to this forty-five second incubation period were inaccurate as a result of red cell stroma interference. Stronger concentrations of saponin would result in only one white cell category, since only the nuclei of all the subpopulations were left. These nuclei have approximately the same size and DNA content thereby inhibiting volumetric or resistivity separation of the white cells into distinct subpopulations.

Another lysing agent, cetrimide (a mixture of quaternary ammonium salts) was tested by prior investigators, resulting in a rough differentiation of white cell subpopulations. See, Hatch, A. and Balazs, T., Am. J. Clin. Path., 36, 220–223 (1960). Further work with cetrimide as a lysing agent illustrated that the choice of the blood diluent played an important role in the results obtained. See D'Angelo, G. and LaCombe, M., "A Practical Diluent for Electronic White Cell Counts", Am. J. Clin. Path., 34, 220–223 (1961). As expected there was interaction not only between the various kinds of blood cells and the lysing reagent, but also between the blood cells and the diluent, the lysing reagent and the diluent, and even the blood proteins and the other three components of the suspension—blood cells, diluent and lysing reagent.

Accordingly, when a further reagent was introduced into certain blood cell analyzers—specifically when, in the 1970's, detergents were introduced into the major diluent or into a wash or blanking line of, for example, those instruments which detected an advancing meniscus level for the purpose of metering the volume of sample suspension which had flowed through the sensor during the analytic cycle—it could be anticipated that there would also be interactions between any introduced detergent and all other components of the diluted blood suspension i.e., blood components (blood cells, blood proteins, blood chemicals and even anticoagulants) and reagents (diluent components, erythrocyte and leukocyte lysate ingredients, hemoglobinometry reagents, and detergent solutions).

This interaction between the environment of blood cells and their ability to maintain their size is well-known. Erythrocytes, because of their lack of granular and nuclear material, are very quickly and dramatically affected by environmental changes; however, it is known that leukocytes and thrombocytes also exhibit this physical environmental response but to a lesser degree.

While the situation is very complex, the main factors that control cell size maintenance in solution are osmolality, pH, conductivity, buffering, ionic size, ionic type, deformation forces, and temperature. Changing one of these parameters can generally be counterbalanced by changing others as well, thus maintaining a solution which keeps the cell volume unchanged. If only one parameter is altered cell volume will usually be affected.

U.S. Pat. Nos. 4,346,018 (filed June 16, 1980), 4,521,518 (filed July 6, 1982) and 4,485,175 (filed Jan. 3, 1983) disclose the use of diluents and lysing agents in the differential volume determination of leukocyte subpopulations. In U.S. Pat. No. 4,485,175, three leukocyte subpopulations (lymphocytes, monocytes, and granulocytes) are differentiated by using a diluent comprising an aqueous solution of procaine hydrochloride, ADA buffer and polynoxylin (dimethylol urea), a distillate of formaldehyde and urea. The lysing agent is described as an aqueous solution of a mixture of quaternary ammonium salts, preferably dodecyltrimethyl ammonium chloride and tetradecyltrimethyl ammonium bromide, and potassium cyanide. The Coulter Counter® Model S Plus is used to obtain volumetric differentiation of the monocyte and granulocyte subpopulations (combination of neutrophils, basophils, and eosinophils) of leukocytes through the significantly slow addition of the lysing agent, in which the quaternary ammonium salts are present in significantly weak concentrations.

The reagents of the instant invention permit quick and accurate cell volume differentiation, resulting in improved exposure of any or all of the infrequent physiologic and rare pathologic white cell subpopulations. The established cetrimide and derivative lytic reagents and methods require mixtures of quaternary ammonium salts to eliminate red cell fragments (and other debris which result from using the lysing agent) for the separation of monocytes from the three (combined) granulocyte subpopulations. By contrast, the lysing solution of the instant invention contains a single quaternary ammonium salt; this is designed to expose infrequent and rare leukocyte subpopulations. This exposure is obtained by carefully controlling the lytic reaction. Under the conditions disclosed herein, better enumeration of the frequent leukocyte subpopulations as well as exposure of the infrequent and rare leukocyte subpopulations is obtained.

Previously known diluents, when used in conjunction with previously known lysing agents, do not unmask the infrequent and rare leukocyte subpopulations adequately. When these reagents are used the frequent lymphocytes and neutrophils tend to obscure the infrequent and rare subpopulations—an overlap inherent to the reagents. Furthermore, the limited monocyte exposure obtained in the prior art is stable only for a very short period of time. The diluent of the instant invention for the first time utilizes 1,3-dimethylurea (a compound very different from the dimethylolurea of U.S. Pat. No. 4,485,175) as a stabilizing agent which allows all the subpopulations of cells to attain a stable condition in a short period of time and to maintain the stability for long periods relative to the analytical cycle time.

Therefore, it is an object of this invention to provide reagents and methods which rapidly arrive at stable resistivity sizes of white cell subpopulations by carefully controlling the lytic reaction, while providing for adequate lysis of the interfering red cells, and their stroma or ghosts.

It is another object of this invention to provide effective reagents and reliable methods which facilitate the enumeration of the frequent lymphocytes and neutrophils while exposing the infrequent and rare leukocyte subpopulations.

It is a further object of this invention to permit accurate hemoglobinometry fast enough for measurement on an automated system simultaneously with white cell measurement.

It is still a further object of this invention to provide reagents and methods which maintain solution conductivity levels which permit good signal-to-noise ratios for blood-cell counting in automated analytical systems.

It is still another object of the instant invention to provide reaction conditions which permit the erythrocytes and thrombocytes to maintain their volume.

SUMMARY OF THE INVENTION

The diluent of the instant invention comprises an isotonically balanced aqueous solution of 1,3-dimethylurea, 1-hydroxypyridine-2-thione, an organic buffer, sodium sulfate, sodium chloride and sodium hydroxide. 1,3-dimethylurea provides a surprising improvement in the stability of all the cell categories, and especially of lysate-modified white cell distributions.

The hematology analyzer detergent of the instant invention is based upon the diluent of the instant invention. The addition of Diazopon (or other wetting agent of the family of polyoxyethylated alkyl phenols or esters) to the diluent provides a detergent which does not introduce volume-disturbing factors into the analyzer system and, further, does not create a foam which could damage the analyzer's internal circuitry.

The lysing agent of the instant invention comprises an aqueous solution of a single quaternary ammonium salt and may contain potassium cyanide. The use of a single salt results in a lysing agent which is easy to manufacture and which, with the specified diluent, provides exposure of the infrequent and rare leukocyte subpopulations heretofore unknown.

Leukocyte subpopulation differentiation in an automated system is made possible by use of the diluent and lysing agent of the instant invention. The method comprises mixing a whole blood sample with the disclosed diluent, adding a lysing agent at extremely slow rates, the lysing agent containing a single quaternary ammonium salt. This method permits accurate enumeration of the lymphocyte and neutrophil subpopulations and sensitive quantitative evaluation of infrequent and rare leukocyte subpopulations.

BRIEF DESCRIPTION OF THE DRAWINGS

FIGS. 2-6 are histograms showing the total number of cells versus cell volume for human samples, which were analyzed according to the methods of instant invention, utilizing a Sequoia-Turner CELL-DYN® 2000 instrument.

DETAILED DESCRIPTION OF THE INVENTION

A. The Reagents

1. The Diluent

Figure 1A:
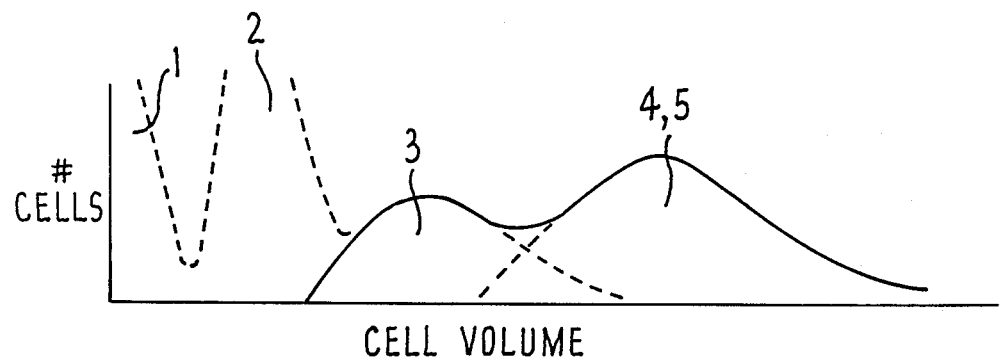
FIGS. 1A and 1B are histograms showing the total number of cells versus cell volume for unmodified and for lysate- and diluent-treated human blood cell samples, respectively.

The diluent comprises an aqueous solution of a cell stabilizing agent, a bacteriocide, an organic buffer and additional ionic components to provide a suitable ionic strength, osmolality, and pH to maintain the volume of erythrocytes and thrombocytes per se, and leukocytes before, during and after interaction with the lysate. A preferred diluent is illustrated in Table 1.

TABLE 1

| Component | Diluent Compositions Range | Preferred |
|---|---|---|
| sodium sulfate | 8–12 grams | 10.0 grams |
| sodium chloride | 3–6 grams | 4.2 grams |
| 1,3 dimethylurea | 0.5–3.0 grams | 1.0 grams |
| 1-hydroxypyridine-2-thione (bacteriocide) | 0.05–2.0 grams | 0.1 grams |
| ADA Buffer (organic buffer) | 0.5–4.0 grams | 1.4 grams |
| sodium hydroxide | to obtain pH = 6.9 | 0.5 grams |
| water | sufficient to make one liter | |

Extensive experimentation with 1,3-dimethylurea and with many other solutes and combinations of solutes demonstrated that the addition of this compound to the diluent gave a degree of stability to the separated white cell subpopulations unattainable in any other way.

Although 1-hydroxypyridine-2-thione is the preferred bacteriostatic agent, others may be substituted so long as the bacteriostatic agent does not substantially adversely interfere with the ionic strength, osmolality, pH or other cell volume determining characteristics, or erythrocyte and leukocyte lysing effects of the reagents used in the automated hematological instrumentation.

pH is conveniently adjusted to 6.9±0.1 with sodium hydroxide, but other bases may be substituted subject to the limitations described above with respect to the bacteriostatic agent.

Sodium sulfate is used to give the proper ionic strength to maintain the erythrocyte volume. Other compounds may be substituted subject to the limitations described with respect to the bacteriostatic agent and sodium hydroxide above.

The diluent osmolality is conveniently adjusted to 320±5 milliosmoles with sodium chloride. The osmolality, once set, must be maintained from batch to batch of a particular version of the diluent, but for a differently constituted, equally acceptable version of diluent, it may be set at a level other than 320±5 milliosmoles.

The organic buffers which may be used in the diluent are ADA [N-(2-acetamido)-2-iminodiacetic acid; N-(carba-moylmethyl)iminodiacetic acid], MOPS [3-(N-Morpholino)propane sulfonic acid], PIPES [piperazine-N,N'-bis(2-ethanesulfonic acid); 1,4-piperazinediethanesulfonic acid], HEPES [N-2-hydroxyethylpiperazine-N'-2-ethanesulfonic acid], BES [N,N-bis(2-hydroxyethyl)2-aminoethanesulfonic acid], BIS-TRIS [bis(2-hydroxyethyl)imino-tris-(hydroxymethyl)methane; 2-bis(2-hydroxy-ethyl)amino-2-(hydroxy-methyl-1,3-propanediol] and TES [(N-tris(hydroxy-methyl)-methyl-2-aminoethane-sulfonic acid); 2-((2-hydroxy-1,1-bis(-hydroxymethyl)ethyl)aminoethane-sulfonic acid)]. The preparation of these organic buffers and others which are useful in the diluent of this invention may be found in a catalog from Cal-Biochem Company, entitled "Biochemical and Immuno Chemical Reagents" La Jolla, Ca. September, 1973.

2. Hematology Analyzer Detergent

Detergents are required for use in hematology analyzers, to ensure repeated accurate results by the removal of excess reagents or sample. They are also used in some analyzers in a photometric volume metering section where the formation of a stable meniscus is vital to instrument precision. Ordinary soaps and detergents are not useful in this context due to several inherent problems. First, the introduction of additional chemical components into the system provides an additional source of background noise which could potentially interfere with accurate hematological analysis. Secondly, the use of conventional soaps and detergents creates a foaming problem within the containers used to supply and store reagents, samples and "washes". The creation of a soapy foam can interfere with the proper volumetric metering of liquid reagents and sample fluids. Also, the foaming problem can cause containers to overflow despite apparently normal liquid levels.

The detergent of the instant invention minimizes all of the above-mentioned difficulties experienced with conventional detergents and soaps. The detergent essentially comprises the components of the above-described diluent with the addition of the wetting agent Diazopon, in amounts of 1–10 ml, preferably 2.5 ml per liter of diluent. Other polyoxyethylated alkyl phenol or ester wetting agents such as Tergitol, Zonyl, Fluorad, etc., are possible.

3. Lysing Agents

In view of several perceived critical parameters for automated hematological analysis, e.g., lytic activity with respect to white cells and the time factor involved in cell stability, we undertook an extensive study of the quaternary salts useful in hematology disclosed in the literature. Particular emphasis was given to the salts present in cetrimide—approximately twenty-five percent dodecyltrimethyl ammonium bromide ($C_{12}$), fifty-five percent tetradecyltrimethyl ammonium bromide ($C_{14}$) and twenty percent hexadecyltrimethyl ammonium bromide ($C_{16}$).

The quaternary salts found useful in the lysing agent have attached to the nitrogen three short chain alkyl groups and one long chain alkyl group. This can be represented by the general formula:

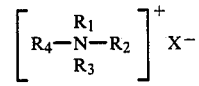

wherein $R_1$, $R_2$ and $R_3$ are short chain alkyl groups, preferably having one to four carbons, and $R_4$ represents long chain alkyl group.

We confirmed the findings of early studies that the higher the carbon number of the long chain alkyl group the more efficient the erythrocyte lysis per unit weight of quaternary ammonium salt. We discovered during these studies that the higher the carbon number of the long chain alkyl group, the more lytic activity there was on the polymorphonuclear cells (granulocytes) whereas the final size of the lymphocytes was relatively unaffected by the carbon number.

We investigated first a $C_{10}$ salt, decyltrimethyl ammonium bromide. Surprisingly, the lytic reaction of this salt was too gentle even at very high concentrations and produced too much red cell stroma to serve any useful purpose as a lytic agent. On the other hand, the $C_{14}$ (tetradecyl) and $C_{16}$ (hexadecyl) homologs were found to affect all the large leukocyte subpopulations too strongly, having approximately the same effect on the frequent neutrophils as on the infrequent monocytes, basophils and eosinophils. The dodecyl ($C_{12}$) homolog was found to be sufficiently strong to lyse the erythrocytes in the disclosed diluent and was uniquely selective in its lytic effect on the various leukocyte subpopulations.

This newly recognized selective tendency of the $C_{12}$ homolog may be explained by two facts (1) the more lipoprotein a cell contains the more the lytic reaction is quenched and (2) the $C_{12}$ homolog is intrinsically gentle enough as a lysate to allow differential quenching of the lytic reaction by the varied content of lipoprotein in the different leukocyte subpopulations.

It is known in the industry and well documented that quenching of lytic reactions may be obtained by the addition of plasma proteins or lipoproteins. The cell groups found in the blood of healthy subjects are the red cell, containing no nucleus or lipoprotein-covered granules, the lymphocyte, containing a small nucleus with no granules, the eosinophil and basophil, each containing a lobulated nucleus and many large granules, the monocyte with a large compact nucleus and few small granules, and the neutrophil containing a lobulated nucleus and very many small granules.

Keeping these differences in cell composition and the quenching phenomenon in mind, one can predict the distributions of leukocyte sizes when the lytic reaction is carefully controlled. The red cells, with only a little external lipoprotein surface area and no granules or nucleus, are lysed completely. The lymphocytes with little lipoprotein surface area are lysed to their nuclei. The larger monocytes, with their more abundant lipoprotein surface area, and the esinophils and basophils, with lobulated nuclei and some granules, are lysed less completely (leaving the nuclei and granules). The neutrophils with their high lipoprotein content tend to resist lysis and remain closest to their original size in vivo.

Figure 1B:
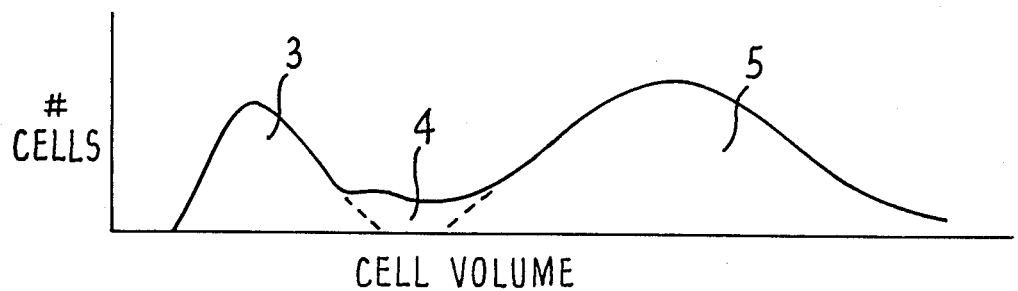

FIG. 1 illustrates the above effect. These histograms show the number of cells plotted versus cell volume. FIG. 1A shows the unmodified leukocyte populations of typical normal human peripheral blood. Thrombocytes (1) and erythrocytes (2) have been greatly reduced in this representation (e.g., by gravity sedimentation). The overlap between frequent lymphocytes (3) and frequent neutrophils (5) completely masks the infrequent and rare leukocyte subpopulations (4). Treatment with the disclosed lysate and diluent results in the distribution shown in FIG. 1B. The lymphocyte and neutrophil subpopulations have become well separated, revealing the infrequent and rare subpopulations between them.

This theoretical insight led to experimentation with dodecyltrimethyl ammonium bromide and dodecyltrimethyl ammonium chloride in various concentrations to determine an optimum for lymphocyte/neutrophil separation. Predictably, the optimum concentration for volumetric separation of the frequent lymphocytes from the frequent neutrophils also resulted in maximum exposure of the infrequent and rare subpopulations in the size region between them. Furthermore, since the typical mature lymphocytes and neutrophils of healthy subjects represent opposite extremes of a differentiation process of immature blood cells into mature circulating leukocytes, it could be predicted theoretically that the lysate combination which resulted in optimal separation of the frequent lymphocytes and neutrophils in typical healthy subjects would also result in good exposure of the anomalous rare immature leukocyte subpopulations which appear in the bloodstream in numerous diseases. This was confirmed experimentally.

The preferred formulation of the lysing agent is shown in Table 2.

TABLE 2

| Lysing Agent Formulations | | |
|---|---|---|
| Component | Range | Preferred |
| dodecyltrimethyl ammonium chloride (50% (w/v) solution) | 55–150 ml | 75 ml |
| potassium cyanide | 0–4 g. | 150 mg |
| water sufficient to make one liter. | | |

The chloride ion in the above table could be replaced by any compatible ion, such as fluoride, bromide, iodide, sulfate, phosphate, nitrate, etc. Some of the preferred quaternary ammonium salts that may replace the dodecyltrimethyl ammonium chloride are:
dodecyltrimethyl ammonium chloride,
dodecyltrimethyl ammonium bromide,
dodecyltrimethyl ammonium fluoride,
dodecyltrimethyl ammonium sulfate,
dodecyldimethylethyl ammonium chloride,
dodecyldimethylethyl ammonium fluoride,
dodecyldimethylethyl ammonium bromide, and
dodecyldimethylethyl ammonium sulfate.

B. Automated Hematological Analysis Methods for Enumerating Leukocyte Subpopulations According to the known operation for the Sequoia Turner CELL-DYN®2000 Automated Hematology Analyzer, which utilizes the instant invention, a mixture of whole blood and diluent is fed into a white cell counting bath, and the strong solution of the gentle lysing agent is added to the same counting bath during more than two seconds of the three-second diluent delivery. In the presence of the 1,3-dimethylurea cell stabilizer, use of our single quaternary ammonium salt permits better separation of the frequent lymphocyte and neutrophil subpopulations providing more consistent enumeration of these as well as of the exposed (by the separation) infrequent and rare leukocyte subpopulations, than was previously available in an electrical resistance particle detection system.

Results

Some of the results of the method herein described are shown in the accompanying figures. These are all leukocyte distribution histograms produced by a Sequoia-Turner, Inc. CELL-DYN®2000 Automated Hematology Analyzer using the preferred formulation of reagents presented above. FIG. 2 shows a normal leukocyte distribution with 76% neutrophils, 20% lymphocytes, and 4% infrequent subpopulations.

FIG. 3 shows the leukocyte distribution from the blood of a patient with a severe deficiency of lymphocytes. The percentages derived from this histogram were 87% neutrophils, 7% lymphocytes, 6% infrequent and rare subpopulations.

FIG. 4 shows a significant population of infrequent and rare cells—7%—coupled with moderately low lymphocytes (15%) and normal neutrophils (78%).

FIG. 5 shows many infrequent and rare cells—10%—in the blood of a patient with a low lymphocyte percentage—11%—and normal neutrophil percentage—79%.

FIG. 6 shows the leukocyte distribution of a patient with a high percentage of lymphocytes (49%) with only 43% neutrophils. Infrequent and rare subpopulations made up the remaining 8% of the population.

Although the foregoing invention has been described in some detail by way of illustration and example for purposes of clarity, it will be obvious to those skilled in the art that certain changes and modifications may be practiced which are intended to be within the scope of the appended claims .

We claim:

1. In a method for volumetrically differentiating leukocytes in a whole blood sample into three subpopulations, identified as lymphocyte, neutrophilic granulocyte and infrequent and rare leukocyte subpopulations, using an atomatic particle analyzing system, said method comprising the steps of:
   (a) supplying a whole blood sample, a volume of diluent suitably balanced for maintaining cell size in the whole blood sample, and a volume of a lysing reagent to an automatic particle analyzing system;
   (b) mixing the whole blood sample with the diluent and the lysing reagent in the automatic particle analyzing system in such a manner as to enable enumeration of the lymphocyte and neutrophilic granulocyte subpopulations in the whole blood sample and to enable quantitative evaluation of the infrequent and rare leukocyte subpopulation in the whole blood sample; and
   (c) using the automatic particle analyzing system to enumerate the lymphocyte and neutrophilic granulocyte subpopulations in the whole blood sample and to quantitatively evaluate the infrequent and rare leukocyte subpopulation in the whole blood sample; wherein the improvements comprise:
   using a diluent containing cell-stabilizing 1,3-dimethylurea and using a lysing agent consisting of 55–150 ml of a 50% (w/v) solution of a single, intrinsically gentle, quaternary ammonium salt, up to 4 g of potassium cyanide, and sufficient water to make one liter, wherein the quaternary ammonium salt is selected from the group consisting of salts having the general formula:

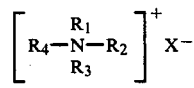

wherein $R_1$, $R_2$ and $R_3$ are short-chain alkyl groups having one to four carbons, $R_4$ is a twelve-carbon alkyl group, and X is a cation selected from the group consisting of halides, sulfates, nitrates, and phosphates.

2. The method of claim 1 wherein said quaternary ammonium salt is a member selected from the group consisting of dodecyltrimethyl ammonium chloride, dodecyltrimethyl ammonium bromide, dodecyltrimethyl ammonium fluoride, dodecyltrimethyl ammonium sulfate, dodecyldimethylethyl ammonium chloride, dodecyldimethylethyl ammonium fluoride, dodecyldimethylethyl ammonium bromide, and dodecyldimethylethyl ammonium sulfate.

3. The method of claim 1 wherein said quaternary ammonium salt is dodecyltrimethyl ammonium chloride.

4. The method of claim 1 wherein said diluent comprises:
   (a) said 1,3-dimethylurea;
   (b) an organic buffer;
   (c) a bacteriostatic agent;
   (d) an inorganic salt to correct conductivity, ionic strength and osmolality in the whole blood sample;
   (e) a suitable additional alkali for pH optimization; and
   (f) water.

5. The method of claim 4 wherein said inorganic salt is a member selected from the group consisting of sodium chloride and sodium sulfate.

6. The method of claim 4 wherein said organic buffer is a member selected from the group consisting of ADA [N-(2-acetamido)-2-iminodiacetic acid; N-(carbamoylmethyl)iminodiacetic acid], MOPS [3-(N-Morpholino)-propane sulfonic acid], PIPES [piperazine-N,N'-bis(2-ethanesulfonic acid); 1,4-piperazinediethanesulfonic acid], HEPES [N-2-hydroxyethylpiperazine-N'-2-ethanesulfonic acid], BES [N,N-bis(2-hydroxyethyl)2-aminoethanesulfonic acid; 2-(bis(2-hydroxy-ethyl)-amino)ethanesulfonic acid], BIS-TRIS [bis(2-hydroxy-ethyl)imino-tris-(hydroxymethyl)methane; 2-bis(2-hydroxy-ethyl)amino-2-(hydroxy-methyl)-1,3-propanediol] and TES [(N-tris(hydroxymethyl)-methyl-2-aminoethane-sulfonic acid); 2-((2-hydroxy-1,1-bis(-hydroxymethyl)ethyl)aminoethanesulfonic acid)].

7. The method of claim 4 wherein said bacteriostatic agent is 1-hydroxypyridine-2-thione.

8. The method of claim 4 wherein said suitable additional alkali for pH optimization is sodium hydroxide.

* * * * *